United States Patent [19]

Jessel, Jr. et al.

[11] Plant 4,122

[45] Oct. 11, 1977

[54] CHRYSANTHEMUM PLANT

[75] Inventors: Walter H. Jessel, Jr., Doylestown; William E. Duffett, Akron, both of Ohio

[73] Assignee: Yoder Brothers, Inc., Barberton, Ohio

[21] Appl. No.: 712,191

[22] Filed: Aug. 6, 1976

[51] Int. Cl.[2] ..... A01H 5/00

[52] U.S. Cl. ..... Plt./79

[58] Field of Search ..... Plt./79

*Primary Examiner*—Robert E. Bagwill

*Attorney, Agent, or Firm*—Donald D. Jeffery

[57] ABSTRACT

A novel chrysanthemum plant of incurved form, with a uniform 10 week flowering response, and the ability to produce quality blossoms during low-light periods.

3 Drawing Figures

The present invention comprises a new and distinct cultivar of *Chrysanthemum morifolium*, Ramat., hereinafter referred to by the cultivar name Marmalade (No. 70212002).

Marmalade is a product of a planned breeding program which had the objective of creating new chrysanthemum cultivars with standard type inflorescence, with uniform 10 week flowering response, with large inflorescence size, with red-bronze and orange-bronze inflorescence color, and with the ability to produce commercially acceptable quality during low light (winter) flowering periods. These traits in combination were not present in previously available commercial cultivars.

Marmalade was originated from a cross made in a controlled breeding program in Barberton, Ohio in 1969. The female, or seed parent, was No. 67015006 (unnamed seedling), a yellow standard originated by the present inventors in 1966 from a cross between No. 64335004 (unnamed seedling) and No. 21610E01 (unnamed seedling). The male, or pollen parent of Marmalade, was No. 621003-1 (unnamed seedling), a bronze standard originated by the present inventors in 1961 from a cross between No. 22005E08 (unnamed seedling) and No. 22005E09 (unnamed seedling). No. 64355004, No. 22005E08, and No. 22005E09 were all products of the breeding program of the present inventors. The parentage of No. 21610E01 is unknown to the present inventors.

Marmalade was discovered and selected as a flowering plant within the progeny of the stated cross by Walter H. Jessel, Jr. and William E. Duffett on Nov. 17, 1970 in a controlled environment in Barberton, Ohio.

The first act of asexual reproduction of Marmalade was accomplished when vegetative cuttings were taken from the initial selection in April, 1971 in a controlled environment in Barberton, Ohio by a technician working under formulations established and supervised by Walter H. Jessel, Jr. and William E. Duffett. Horticultural examination of selected units initiated Mar. 2, 1972 has demonstrated that the combination of characteristics as herein disclosed for Marmalade are firmly fixed and are retained through successive generations of asexual reproduction.

Marmalade has not been observed under all possible environmental conditions. The phenotype may vary significantly with variations in environment such as temperature, light intensity, and daylength. The following observations, measurements, and comparisons describe plants grown in Barberton, Ohio under greenhouse conditions which closely approximate those generally used in commercial practice, as described in Chart A which appears at the end of the present specification. A light intensity chart of general use is shown in ASHAE TRANS., Vol. 64, pg. 64, and reference is made thereto.

The following traits have been repeatedly observed and are determined to be basic characteristics of Marmalade which in combination distinguish this chrysanthemum as a new and distinct cultivar:

1. Incurved inflorescence form.
2. Standard inflorescence type.
3. Red-bronze to orange-bronze inflorescence color.
4. Very tall plant height (requires 1–2 long day weeks as single stem plant prior to short days to attain a total height as a flowering plant of 72 to 82 cm. during the period from October through May).
5. Uniform ten week flowering response to photoperiodic short day control.
6. Diameter across face of inflorescence up to 18 cm. at maturity.

The accompanying photographic drawings show typical inflorescence and foliage characteristics of Marmalade with colors being as nearly true as possible with illustrations of this type. Sheet 1 is a color photograph of Marmalade. Sheet 2 is a black and white photograph of the inflorescence of Marmalade. Sheet 3 is a black and white photograph showing the foliage of Marmalade at three stages of growth.

Of the many commercial cultivars known to the present inventors, the most similar existing cultivar in comparison to marmalade is Gambit (No. 67406003; U.S. Plant Pat. No. 3,481). Reference is made to attached Chart B which compares certain characteristics of Marmalade to those same characteristics of Gambit. It will be noted that Marmalade has darker inflorescence color, greater diameter across face of inflorescence, taller plant height, longer flowering response period, and greater tolerance of ray floret shatter than Gambit. The inflorescence form and inflorescence type of Gambit are similar to those same characteristics of Marmalade.

In the following description, color references are made to The Munsell Color Cascade, 1972 edition. The color values were determined between 9:30 and 10:00 A.M. on May 17, 1976 under 150 foot-candle light intensity at Barberton, Ohio.

Botanical classification: *Chrysanthemum morifolium,* Ramat. cv. Marmalade.

INFLORESCENCE

Capitulum (See Sheets 1 and 2 of drawings):

*Form.*—Incurved.

*Type.*—Standard.

*Diameter across face.*—150 to 180 mm.

Corolla of ray florets:

*Persistence.*—Resists shatter.

*Color (abaxial).*—34-13 over 30-6 to 29-12 over 29-4.

*Color (adaxial).*—29-12 over 28-9 to 29-10 over 29-4.

Reproductive organs:

*Androecium.*—Scarce; present disc florets only; scant pollen.

*Gynoecium.*—Present both ray and disc florets.

PLANT

General appearance: Semi-upright branching pattern; very tall height.

Foliage (See Sheets 1 and 3 of drawings):

*Color (abaxial).*—Approximately 19-14 to 19-15.

*Color (adaxial).*—Approximately 20-14 to 19-14.

CHART A

AVERAGE GREENHOUSE CHRYSANTHEMUM ENVIRONMENTS USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7–10 f.c. | To Sept. 15 on - 5:30 PM Off - 7:30 AM | From Oct. 15 300 ppm |
| WINTER | 58° F to 62° F | 65° F to 70° F | 60° F to 65° F | 2 to 5 weeks at 5 hours Per Night of 7–10 f.c. | NONE | 300 ppm |
| SPRING | 58° F to 65° F | 65° F to 80° F | 60° F to 75° F | 2 to 4 weeks at 5 Hours Per Night of 7–10 f.c. | From Mar. 15 on - 5:30 PM Off - 7:30 AM | To Apr. 15 300 ppm |
| SUMMER | 62° F to 68° F | 70° F to 90° F | 65° F to 75° F | 1 to 2 weeks at 3 Hours Per Night of 7–10 f.c. | on - 6:00 PM Off - 8:00 AM | NONE |

CHART B

COMPARISON OF MARMALADE AND GAMBIT

| CULTIVAR | INFLORESCENCE COLOR | INFLORESCENCE FORM AND TYPE | DIAMETER ACROSS FACE OF INFLORESCENCE | PLANT HEIGHT | FLOWERING RESPONSE PERIOD | TOLERANCE OF SHATTER |
|---|---|---|---|---|---|---|
| Marmalade | Red-Bronze to Orange-Bronze | Incurved Standard | 160 to 180 mm | Very tall | 10 week | Good |
| Gambit | Golden-Bronze | Incurved Standard | 145 to 160 mm | Tall | 9 week | Poor |

COMPARISONS MADE OF PLANTS GROWN IN A GREENHOUSE IN BARBERTON, OHIO UNDER CONDITIONS AS DESCRIBED IN CHART A.

We claim:

1. A new and distinct cultivar of *Chrysanthemum morifolium,* Ramat. plant to be known by the cultivar name Marmalade and particularly characterized as to uniqueness by the combined characteristics of incurved inflorescence form, standard inflorescence type, red-bronze to orange-bronze inflorescence color, very tall plant height, uniform 10 week flowering response to photoperiodic short day control, and diameter across face of inflorescence up to 18 cm. at maturity.

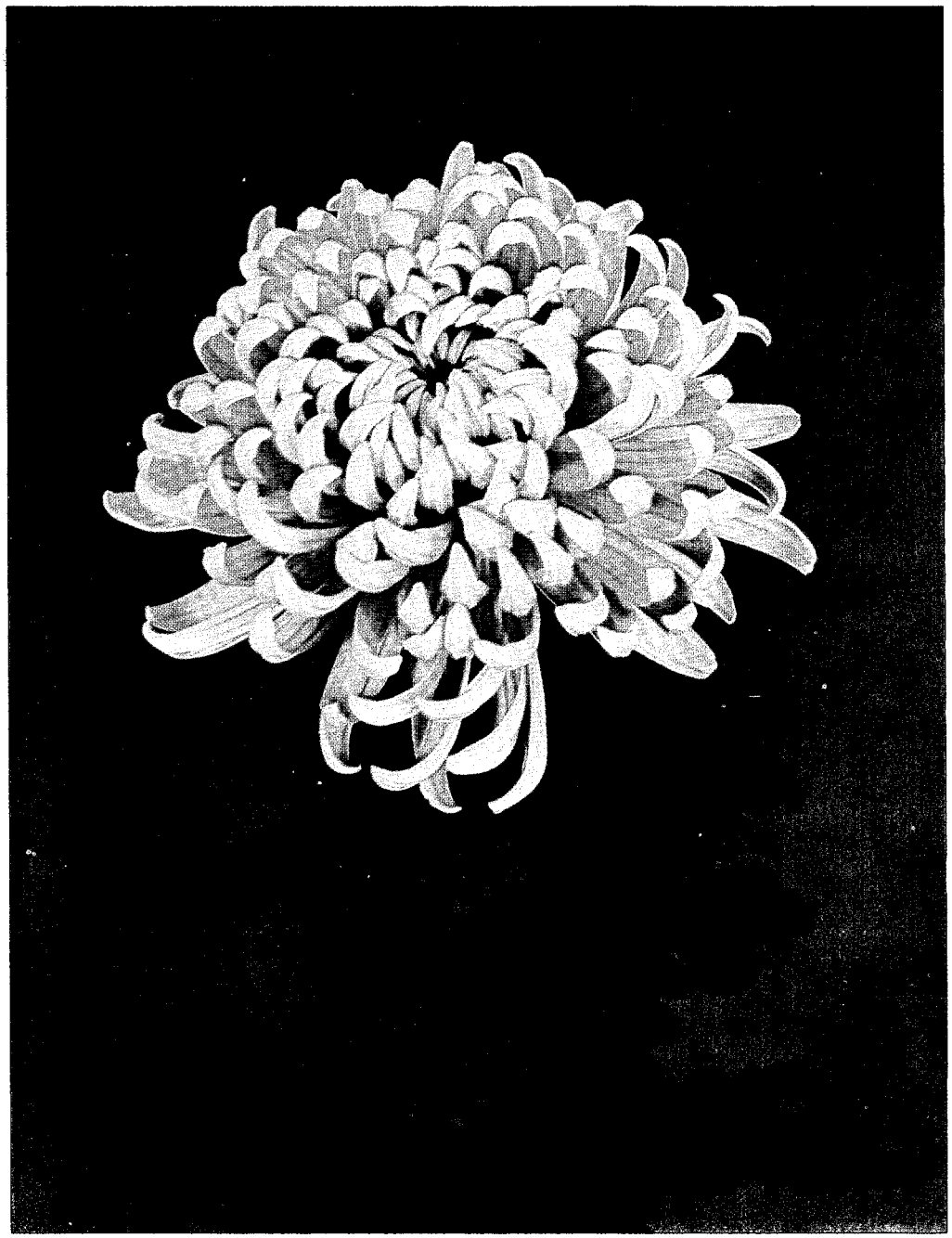

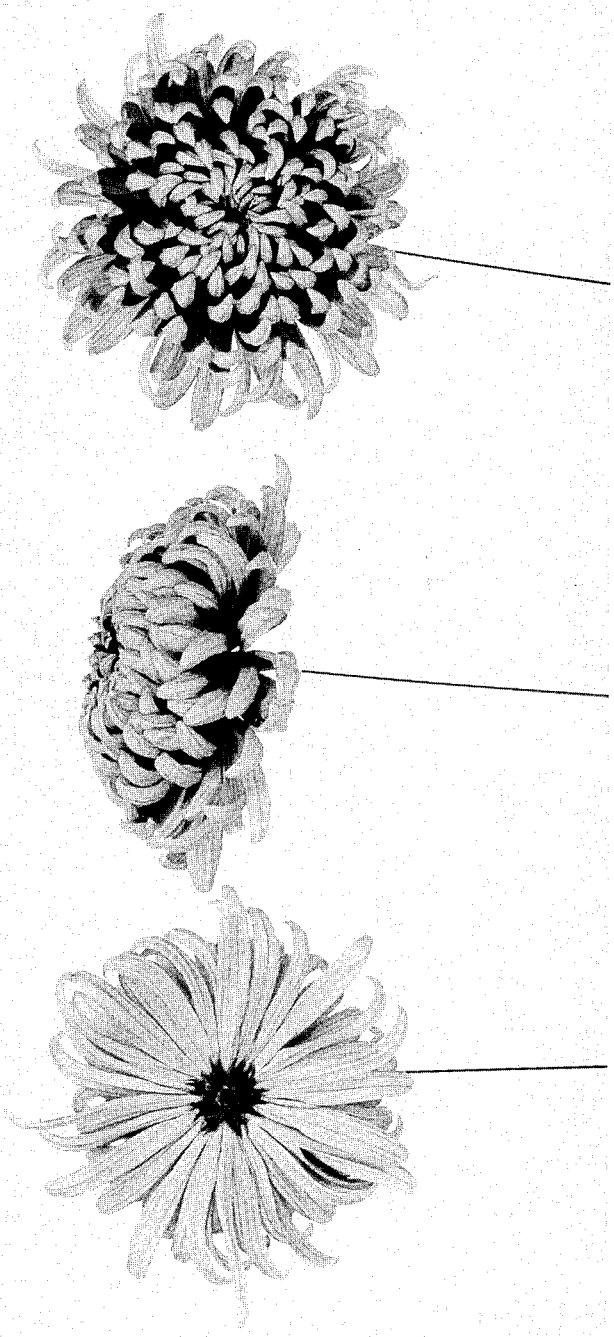

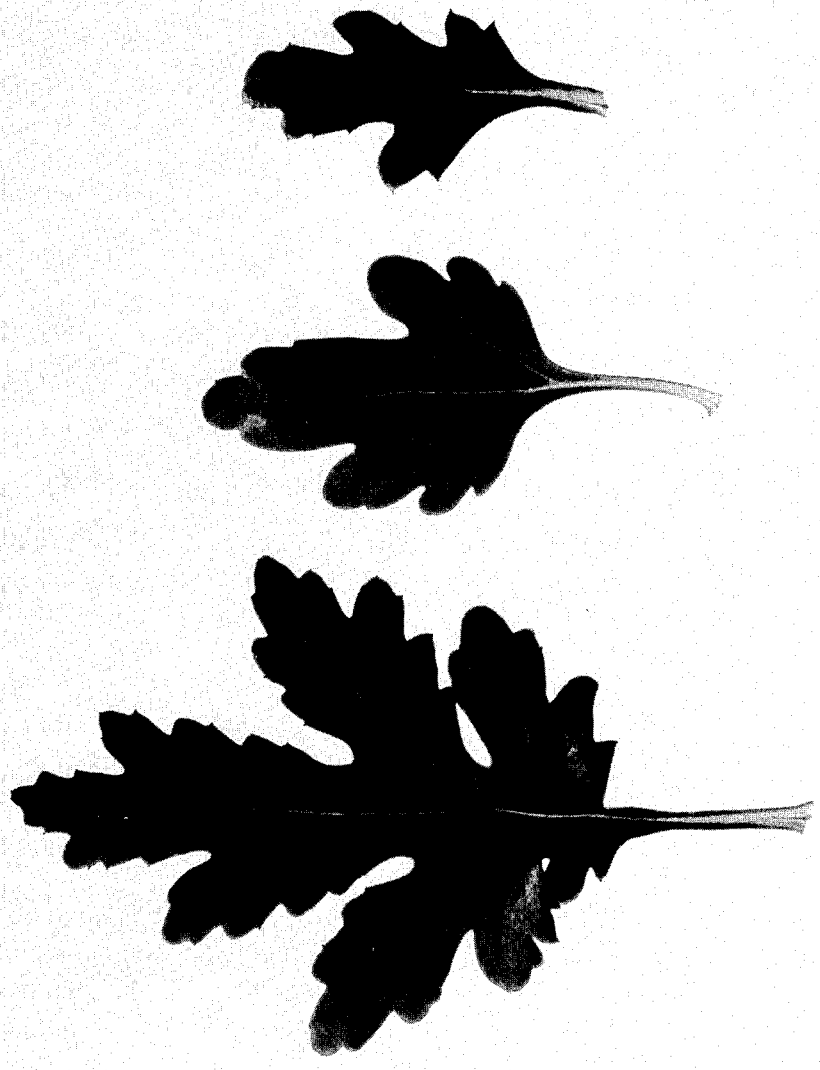

* * * * *